(12) United States Patent
Larsen et al.

(10) Patent No.: US 7,903,252 B2
(45) Date of Patent: Mar. 8, 2011

(54) NOISE CANCELLATION IN FOURIER TRANSFORM SPECTROPHOTOMETRY

(75) Inventors: David W. Larsen, St. Charles, MO (US); Zhi Xu, St. Louis, MO (US)

(73) Assignee: The Curators of the University of Missouri, St. Louis, MO (US)

( * ) Notice: Subject to any disclaimer, the term of this patent is extended or adjusted under 35 U.S.C. 154(b) by 548 days.

(21) Appl. No.: 11/845,580

(22) Filed: Aug. 27, 2007

(65) Prior Publication Data

US 2007/0291255 A1 Dec. 20, 2007

Related U.S. Application Data

(63) Continuation-in-part of application No. 11/035,034, filed on Jan. 13, 2005, now Pat. No. 7,262,844.

(51) Int. Cl.
G01B 9/02 (2006.01)
G01J 3/45 (2006.01)
G01N 21/00 (2006.01)

(52) U.S. Cl. .......................................... 356/451

(58) Field of Classification Search .................. 356/319, 356/433, 451, 517
See application file for complete search history.

(56) References Cited

U.S. PATENT DOCUMENTS

| | | | |
|---|---|---|---|
| 3,753,619 A * | 8/1973 | Thorpe et al. ................. | 356/451 |
| 3,877,817 A | 4/1975 | Ralston | |
| 3,939,348 A * | 2/1976 | Barrett ...................... | 250/339.13 |
| 3,950,101 A * | 4/1976 | Dewey, Jr. ...................... | 356/51 |
| 4,059,405 A | 11/1977 | Sodickson et al. | |
| 4,070,111 A | 1/1978 | Harrick | |
| 4,176,957 A | 12/1979 | Maeda et al. | |
| 4,181,441 A | 1/1980 | Noller et al. | |
| 4,213,703 A | 7/1980 | Haunold et al. | |
| 4,518,700 A | 5/1985 | Stephens | |
| 4,565,447 A | 1/1986 | Nelson | |
| 4,594,510 A * | 6/1986 | Brown et al. ............ | 250/339.13 |
| 4,781,456 A | 11/1988 | Nogami | |
| 4,823,168 A | 4/1989 | Kamahori et al. | |
| 4,848,904 A * | 7/1989 | Sapp et al. ..................... | 356/319 |
| 4,849,637 A * | 7/1989 | Cerff et al. ..................... | 250/345 |
| 4,922,309 A | 5/1990 | Sekiwa et al. | |
| 4,929,078 A | 5/1990 | Harmon | |

(Continued)

FOREIGN PATENT DOCUMENTS

AU 730982 B2 3/2001

(Continued)

OTHER PUBLICATIONS

Product Catalog 2003, Ocean Optics, Inc.

(Continued)

*Primary Examiner* — Gregory J Toatley
*Assistant Examiner* — Scott M Richey
(74) *Attorney, Agent, or Firm* — Senniger Powers LLP

(57) ABSTRACT

Increasing signal to noise ratio in optical spectra obtained by spectrophotometers. An interferometer introduces interference effects into a source light beam. A dual beam configuration splits the source beam having the interference effects into a reference beam and a sample beam. The reference beam interacts with a reference substance and is detected by a reference detector. The sample beam interacts with a sample substance and is detected by a sample detector. An optical spectra of the sample is based on the difference between the detected reference beam and the detected sample beam.

18 Claims, 14 Drawing Sheets

U.S. PATENT DOCUMENTS

| | | | | |
|---|---|---|---|---|
| 4,931,660 | A * | 6/1990 | Mayer | 250/575 |
| 5,029,276 | A | 7/1991 | Buehler et al. | |
| 5,064,283 | A | 11/1991 | Tober | |
| 5,110,211 | A * | 5/1992 | Niki et al. | 356/451 |
| 5,134,276 | A | 7/1992 | Hobbs | |
| 5,251,008 | A | 10/1993 | Masutani | |
| 5,255,075 | A * | 10/1993 | Cush | 356/445 |
| 5,376,783 | A | 12/1994 | Vecht et al. | |
| 5,434,412 | A | 7/1995 | Sodickson et al. | |
| 5,499,095 | A | 3/1996 | Gast et al. | |
| 5,540,825 | A | 7/1996 | Yeung et al. | |
| 5,628,891 | A | 5/1997 | Lee | |
| 5,680,209 | A | 10/1997 | Machler | |
| 5,715,056 | A * | 2/1998 | Urabe et al. | 356/451 |
| 5,742,200 | A | 4/1998 | He | |
| 5,745,243 | A | 4/1998 | Wilcox et al. | |
| 5,784,158 | A | 7/1998 | Stanco et al. | |
| 5,943,136 | A | 8/1999 | Pipino et al. | |
| 6,002,477 | A | 12/1999 | Hammer | |
| 6,040,914 | A | 3/2000 | Bortz et al. | |
| 6,097,034 | A | 8/2000 | Weckstrom et al. | |
| 6,108,083 | A | 8/2000 | Machler | |
| 6,207,369 | B1 | 3/2001 | Wohlstadter et al. | |
| 6,243,170 | B1 | 6/2001 | Ershov | |
| 6,249,348 | B1 | 6/2001 | Jung et al. | |
| 6,555,820 | B1 * | 4/2003 | Tacke et al. | 250/339.01 |
| 6,605,808 | B2 * | 8/2003 | Mickan et al. | 250/341.8 |
| 6,667,805 | B2 | 12/2003 | Norton et al. | |
| 6,741,348 | B2 * | 5/2004 | Larsen et al. | 356/319 |
| 6,903,818 | B2 | 6/2005 | Cerni et al. | |
| 7,099,003 | B2 | 8/2006 | Saptari et al. | |
| 7,206,078 | B2 * | 4/2007 | Pfaff et al. | 356/517 |
| 7,248,357 | B2 * | 7/2007 | Servaites et al. | 356/306 |
| 7,262,844 | B2 * | 8/2007 | Larsen et al. | 356/319 |
| 7,352,463 | B2 * | 4/2008 | Bounaix | 356/437 |
| 7,352,469 | B2 * | 4/2008 | McGrew | 356/451 |
| 7,450,239 | B2 * | 11/2008 | Uehara et al. | 356/451 |
| 7,542,147 | B2 * | 6/2009 | Demarest | 356/487 |
| 7,710,573 | B2 * | 5/2010 | Toury et al. | 356/450 |
| 2003/0202179 | A1 | 10/2003 | Larsen et al. | |
| 2004/0145741 | A1 * | 7/2004 | Cole et al. | 356/436 |
| 2005/0036146 | A1 * | 2/2005 | Braig et al. | 356/436 |
| 2006/0152726 | A1 | 7/2006 | Larsen et al. | |
| 2006/0262317 | A1 * | 11/2006 | Doak et al. | 356/451 |
| 2008/0285601 | A1 * | 11/2008 | Sherrer et al. | 372/19 |
| 2009/0180122 | A1 * | 7/2009 | Federici | 356/451 |
| 2010/0001189 | A1 * | 1/2010 | Federici | 250/340 |

FOREIGN PATENT DOCUMENTS

| | | |
|---|---|---|
| JP | 06053919 A | 2/1994 |
| JP | 7-333149 | 12/1995 |
| JP | 11271219 | 10/1999 |
| JP | 2001194295 | 7/2001 |
| WO | 9007132 | 6/1990 |
| WO | 97/09607 | 3/1997 |
| WO | 01/07881 A1 | 2/2001 |

OTHER PUBLICATIONS

Kurt L. Haller and Philip C.D. Hobbs, "Double Beam Laser Absorption Spectroscopy: Short Noise-Limited Performance at Baseband with a Novel Electronic Noise Canceller," SPIE, vol. 1435, Optical Methods for Ultrasensitive Detection and Analysis: Techniques and Applications, 1991, pp. 298-309.

Extended Search Report Issued in European Patent Application No. EP 06 717 941, dated May 20, 2009, 7 pages.

Supplemental European Search Report Issued in European Patent Application No. EP 03726186.4, dated Sep. 22, 2009, 6 pages.

International Search Report and Written Opinion issued in PCT/US08/73659 dated Oct. 22, 2008, 10 pages.

* cited by examiner

NOISE CANCELLATION IN FOURIER TRANSFORM SPECTROPHOTOMETRY

CROSS-REFERENCE TO RELATED APPLICATION

This application is a continuation-in-part of co-pending U.S. patent application Ser. No. 11/035,034, filed Jan. 13, 2005, entitled "Ultrasensitive Spectrophotometer," the entire disclosure of which is incorporated herein by reference.

BACKGROUND

A fundamental property of a sample, be it gas, liquid or solid, is its tendency (or lack of tendency) to affect light at certain wavelengths. Characterization of the tendency of a sample to absorb, scatter, or transmit light is the basis for spectrophotometry. Exemplary applications of spectrophotometry include chemical and biological sample analysis. Other exemplary applications include manufactured product testing and the testing of air or water quality.

One significant aspect of any application of quantitative spectrophotometry is the ability to numerically characterize a sample. Thus, quantitative spectrophotometry reveals sample properties and allows one sample to be differentiated from another. In particular, aspects of spectrophotometry are often applied to determine optical spectra for samples in order to generally characterize and distinguish the samples. For example, aspects of spectrophotometry may be used to determine an absorption spectrum and/or a transmittance spectrum of a sample for identifying the sample or differentiating it from another sample. A sample's absorption spectrum indicates the fraction of light absorbed by the sample for a particular range of wavelengths. A sample's transmittance spectrum indicates the faction of light which passes through the sample for a particular range of wavelengths. The range of wavelengths may include one or more of the following ranges of light: ultraviolet (UV), visible, and infrared (IR).

Two general methods by which optical spectra, such as absorption and transmittance spectra, are obtained are (i) dispersive scanning (hereinafter referred to as "DS") and (ii) Fourier Transform (hereinafter referred to as "FT"). Both methods include facilitating an interaction between a sample light beam and a sample and detecting light (e.g., transmitted light, reflected light, scattered light) resulting from the interaction. Similarly, both methods include facilitating an interaction between a light beam and a reference or a sample, and detecting light (e.g., transmitted light, reflected light, scattered light) resulting from the interaction. For both methods, an optical spectrum is obtained from the ratio of the detected light for the sample to the detected light for the reference. According to the DS method, the sample light beam and the reference light beam each contain light having one particular wavelength (or a very narrow waveband) referred to as, monochromatic light. Thus, to obtain an optical spectrum, the DS method includes selecting the particular wavelength (or very narrow waveband) from a wavelength range, facilitating the sample and reference interactions with light, detecting the resulting light, and repeating the process for each particular wavelength in the wavelength range.

According to the FT method, however, the sample light beam and the reference light beam contain light having a plurality of wavelengths (e.g., polychromatic light). To obtain an optical spectrum, the FT method includes modulating the sample light beam and the reference light beam, facilitating the sample and reference interactions with light, detecting the resulting light, and applying Fourier Transform techniques to the detected light. The FT method, instrumentation, and operation thereof are described in further detail below.

In general, the DS method and the FT method can be applied to the entire light spectrum (e.g., electromagnetic spectrum). However, the FT method is generally preferable to the DS method for infrared and near infrared applications because it produces substantially enhanced signal to noise ratios with respect to DS methodology. Additionally, since the FT method obtains the optical spectrum from exposing the sample and reference to only one light beam, rather than a plurality of light beams, the optical spectrum is generally obtained in a substantially shorter time using the FT method rather than the DS method. Thus, the FT method is often more desirable than the DS method when spectra must be obtained quickly or when certain physical features of the sample must be enhanced.

Irrespective of whether optical spectra are obtained using the DS method or the FT method, sensitivity, precision, and accuracy of the spectrophotometric measurements are critical. The sensitivity of a spectrophotometric measurement directly relates to the ability to detect small differences between samples having similar absorption properties. The greater the sensitivity, the smaller the difference that can be detected. The precision of a spectrophotometric measurement may be considered as a function of the ability to repeat the same measurement for an identical sample at different times. The accuracy of a spectrophotometric measurement may be considered as a function of the ability to correctly determine the numerical measure of the sample composition. The latter is critical, for example, when attempting to quantify an unknown element in a sample. Over a given range of concentration, the quantification is characterized by certain levels of precision and accuracy. However, below some critical lower limit of the concentration range, both precision and accuracy are adversely affected. This lower limit is the detection limit of the particular spectrophotometric instrument. As sensitivity increases, the detection limit decreases. Improvements in sensitivity, while retaining high levels of precision and accuracy are desirable.

For example, in FT methods, fluctuations in the light source power cause noise in the signal generated by the detector. The noise is ultimately carried through to the optical spectrum (e.g., transmittance spectrum). Additionally or alternatively, in FT methods, the various noises include digitization errors and tracking errors. In particular, digitization errors are a result of the finite resolution of the digitizer (i.e., electronics module, such as, analog to digital converter) limiting the ability of the digitizer to digitize signals generated by the detector with sufficient precision to indicate relatively small absorption peaks. This noise is introduced into the electronic signal at the stage of analog to digital conversion. Tracking errors are a result of the inconsistent sampling associated with the timing of the modulations introduced into the input light beam by an interferometer. The noise is ultimately carried through to the optical spectrum (e.g., transmittance spectrum). Such noise sources have traditionally not been considered in conventional devices that were incapable of providing the sensitivity required to make such sources apparent.

SUMMARY

Embodiments of the present invention overcome one or more deficiencies of conventional spectrophotometers by providing a spectrophotometry system which procures ultrasensitive measurements of light intensity. In particular, aspects of the present invention increase the signal to noise ratio in optical spectra obtained by Fourier Transform methods. Embodiments of the present invention include a spectrophotometry system having a dual beam configuration for producing a sample and a reference beam. The dual beams are derived from the same light source, so that noise associated with the light source, both relatively fast random fluctuation and slower drift, will appear coherently in both beams. Aspects of the invention advantageously cancel the coherent noise and thus increase sensitivity of measurements made by the spectrophotometry system.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

Aspects of the invention provide for spectrophotometric measurements that address potential interferences (e.g., noise) from various sources. The various noise sources include noise fluctuations of the light source, airborne particulates in the beam paths, bubbles and suspended particulates in liquids under study, reflections from light detector surfaces, and the like.

Figure 1:
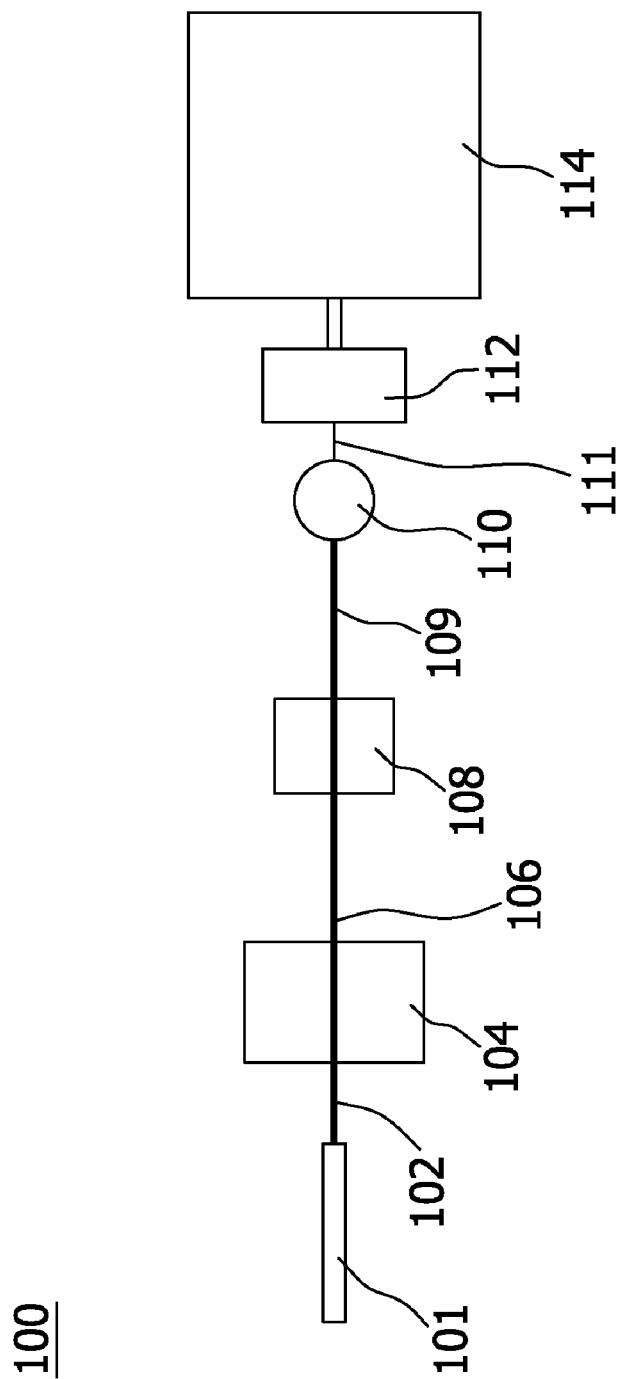
FIG. 1 is an exemplary block diagram illustrating a spectrophotometry system having a single beam configuration.

FIG. 1 illustrates instrumentation 100 for performing the FT method. The FT instrumentation 100, as generally known in the art, has a single beam configuration. In operation of this FT instrumentation, a light source 101 produces polychromatic light 102 that enters an interferometer 104. The interferometer 104 introduces interference effects that are reflected in an output beam 106. In particular, the interferometer 104 modulates each individual wavelength component of the input light beam 102. Because the input light beam 102 covers a range of wavelengths, the effect of the interferometer on the total light beam can be described as a sum of the modulations for all the wavelength components in the input light beam 102. The result is an output beam 106 having a complex pattern, referred to as an interferogram, encoding each frequency (or wavelength component) included in the input light beam 102. The output beam 106 enters a Sample/Reference compartment 108 and interacts with a sample or a reference substance. For example, the output beam 106 may be transmitted through or reflected off of the sample/reference substance. Accordingly, the resulting beam 109 corresponds to a resulting interferogram, which characterizes optical properties of the sample/reference substance at each of the frequencies (or wavelength components) that were included in the input light beam 102. The resulting beam 109 strikes a detector 110. And the detector 110 generates a signal that is fed along path 111. The signal is representative of the resulting beam 109 and thereby representative of the resulting interferogram.

Figure 2:
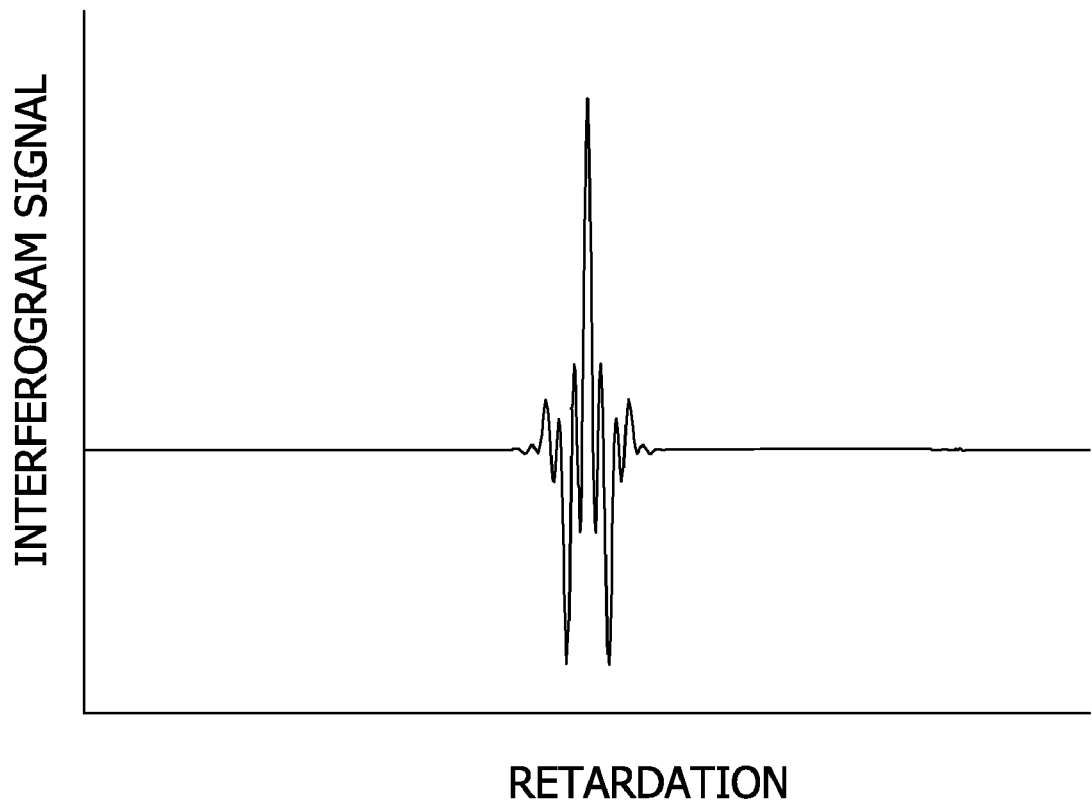
FIG. 2 is a plot of an exemplary interferogram.

The FT instrumentation 100 generally includes or is used in conjunction with a computer 114 to display and/or analyze spectral data. Accordingly, the detector signal is fed via path 111, through an electronics module 112 to the computer 114. In particular, the signal 111 from detector 110 is digitized at a particular sampling frequency and processed by computer 114 to compute the resulting interferogram. FIG. 2 illustrates an exemplary interferogram computed and displayed by computer 114. For example, computer 114 performs a discrete Fourier Transform operation, DFT, on the resulting interferogram to compute an optical spectrum for the sample/reference substance located in the Sample/Reference compartment 108.

Figure 3:
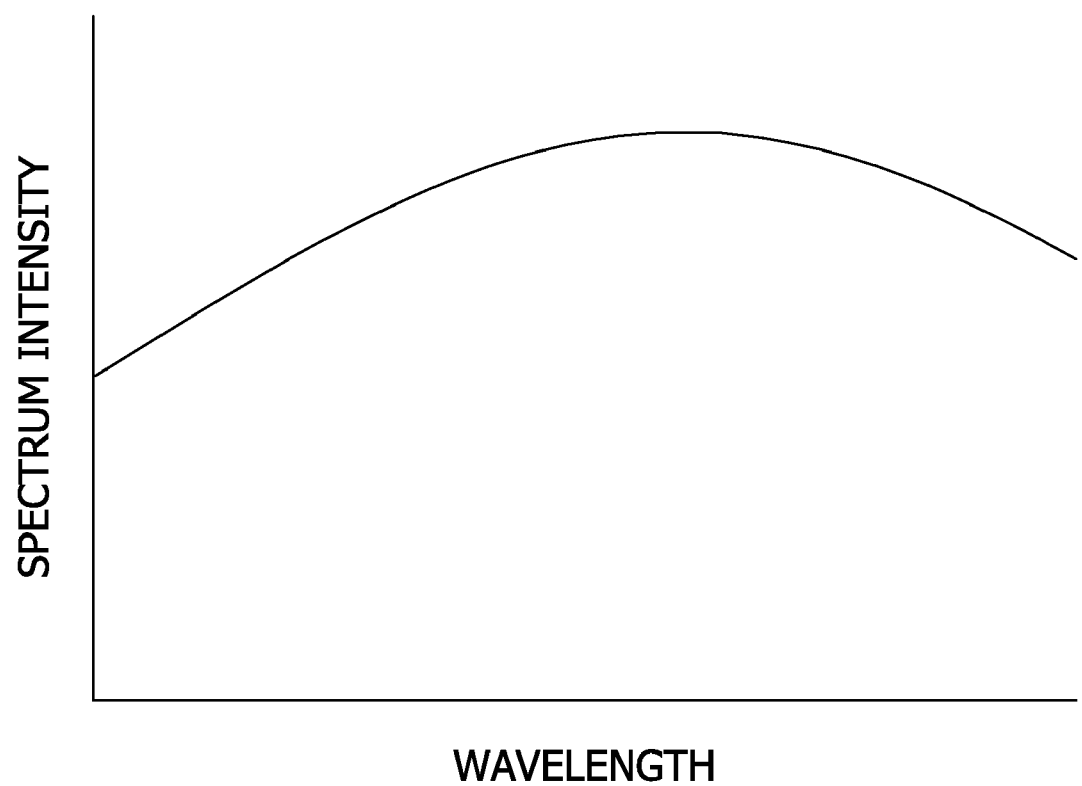
FIG. 3 is an exemplary spectrum intensity plot for a background spectrum.
Figure 4:
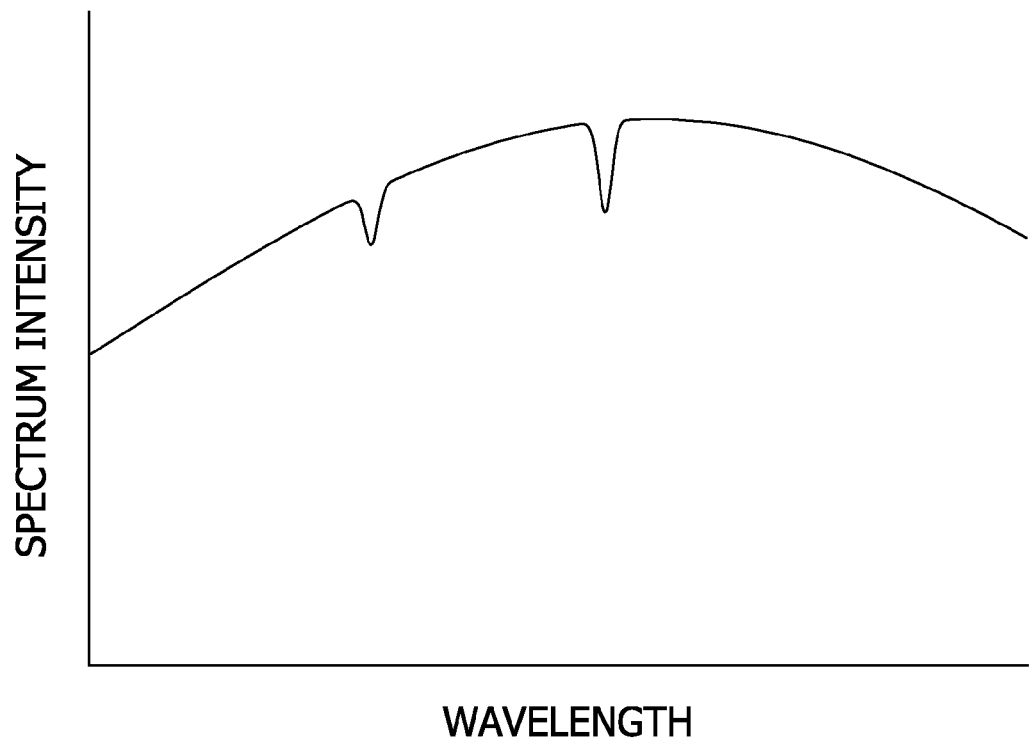
FIG. 4 is an exemplary spectrum intensity plot for a sample spectrum.

To obtain a transmittance spectrum, FT instrumentation 100 performs the described procedure twice, once to obtain a background spectrum ($G_B$), and once to obtain a sample spectrum ($G_S$) and then compares the two obtained spectra ($G_B$ and $G_S$). The background spectrum ($G_B$), also referred to as a reference spectrum, is the spectrum of light directed to detector 110 under reference conditions. FIG. 3 illustrates a spectrum intensity plot for an exemplary background spectrum $G_B$. The sample spectrum, ($G_S$), is the spectrum of light directed to detector 110 in the presence of the sample in the Sample/Reference compartment 108. FIG. 4 illustrates a spectrum intensity plot for an exemplary sample spectrum Gs. The reference conditions include a reference (or background) present in the Sample/Reference compartment 108 for interacting with the light beam 106. In general, the reference and sample may have the form of a solid, liquid or gas. The reference is selected to have attributes that can be used for analyzing the sample. For example, the reference may be a solid, liquid, or gas, which is substantially identical to the sample but for a particular component. A comparison between the sample and the reference spectra reveals information about the particular component inasmuch as the differences in the spectra are due to the particular component. Alternatively, the reference consists of air in which case there is no additional substance in the Sample/Reference compartment 108. When there is no additional substance in the Sample/Reference compartment 108, there are no effects attributable to the sample in the background spectrum ($G_B$). Thus, a comparison between the sample and reference spectra reveals information about the sample substance, rather than just one component thereof.

Figure 5:
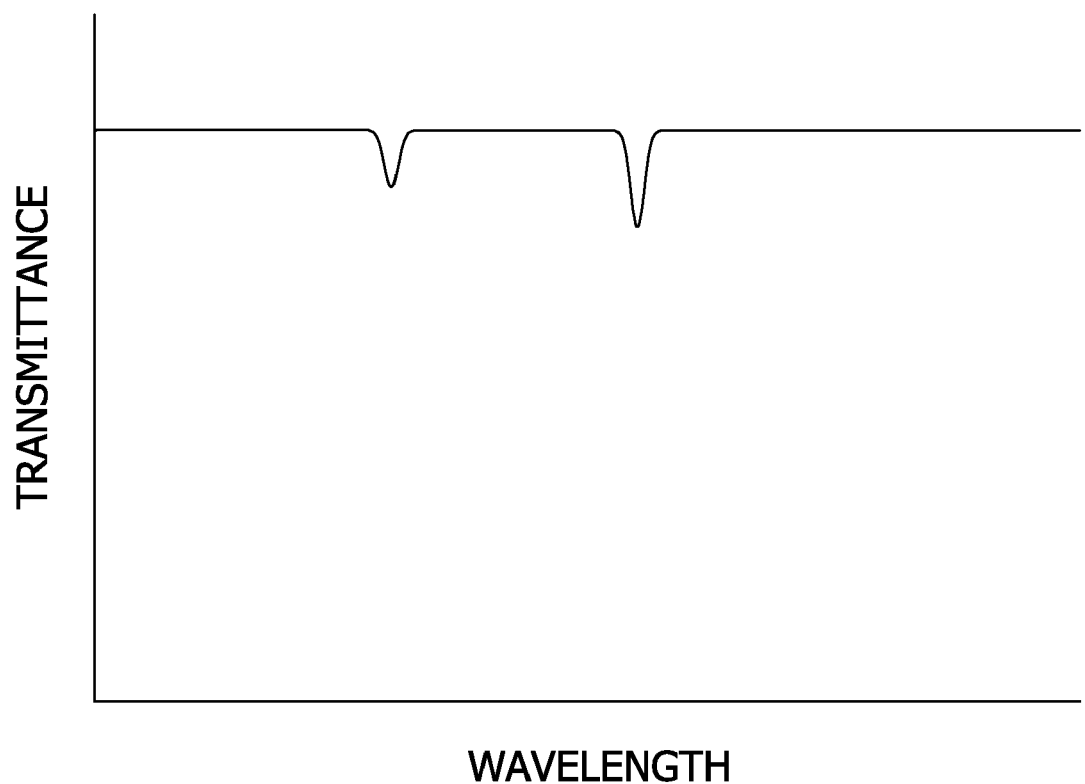
FIG. 5 is an exemplary transmittance spectrum plot.

The transmittance spectrum is obtained by rationing the sample spectrum against the background (i.e., $G_S/G_B$). Because the spectra are discrete, the ratio is taken point wise at each frequency, for all of the frequencies represented. FIG. 5 illustrates a transmittance spectrum based on the exemplary background spectrum plotted in FIG. 3 and the exemplary sample spectrum plotted in FIG. 4. Transmittance is defined as unity (or 100%), when there is no absorbance by the sample. Thus, a transmittance value less than one indicates absorption by the sample at the frequency (or wavelength) of the transmittance value.

As described above, irrespective of whether the optical spectra are obtained using the DS method or the FT method, sensitivity, precision, and accuracy of the spectrophotometric measurements are critical. For example, in FT methods, fluctuations in the light source power cause noise in the signal generated by detector 110. The noise is ultimately carried through to the optical spectrum (e.g., transmittance spectrum). Additionally or alternatively, in FT methods, the various noises include digitization errors in the interferogram and tracking errors with the interferometer 104. In particular, digitization errors are a result of the finite resolution of the digitizer (i.e., electronics module, such as, analog to digital converter) limiting the ability of the digitizer to digitize signals generated by the detector with sufficient precision to indicate relatively small absorption peaks. This noise is introduced into the electronic signal at the stage of analog to digital conversion. Tracking errors are a result of the inconsistent sampling associated with the timing of the modulations introduced into the input light beam by an interferometer. The noise is ultimately carried through to the optical spectrum (e.g., transmittance spectrum). Such noise sources have traditionally not been considered in conventional devices that were incapable of providing the sensitivity required to make such sources observable.

Embodiments of the invention include a spectrophotometry system having a dual light beam configuration with sample and reference beams. According to a dual light beam configuration, the dual beams are derived from the same light source, so that experimental noise associated with the light source, both relatively fast random fluctuation and slower drift, will appear coherently in both beams. Embodiments of the present invention reduce the level of the coherent experimental noise by use of a cancellation technique and thereby improve sensitivity. Sample and reference detectors respectively generate signals representative of the sample and reference beams, and the coherent fluctuations are canceled by taking the difference in the generated signals by use of appropriate electronic circuitry.

In one embodiment, the present invention includes a spectrophotometry system, having a dual light beam configuration, for employing the DS method. Such an embodiment is described in further detail in the '726 application. Additionally, aspects related to noise occurring in spectrophotometry systems are described in U.S. Pat. No. 6,741,348 entitled "Ultrasensitive Spectrophotometer", the entire disclosure of which is incorporated herein by reference.

Figure 6:
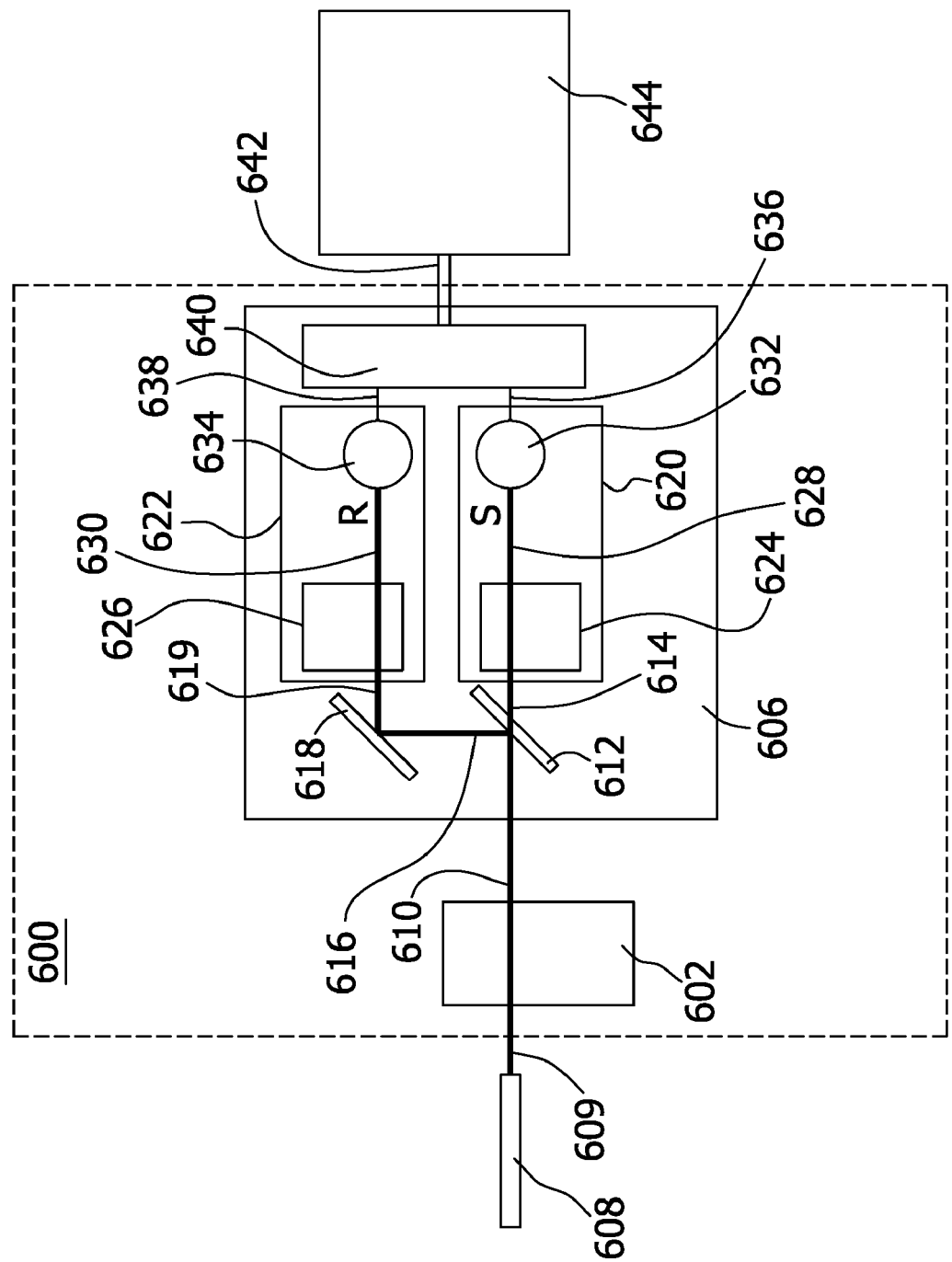
FIG. 6 is a block diagram illustrating a spectrophotometry system, having a dual light beam configuration for employing the Fourier Transform method according to an embodiment of the invention.

In another embodiment, represented by the block diagram in FIG. 6, the present invention includes a spectrophotometry system 600, having a dual light beam configuration, for employing the FT method. In particular, the spectrophotometry system 600 includes an interferometer 602 and a module 606. The interferometer 602 receives a source light beam 609 generated by a light source 608 and produces an output beam 610 having interference effects.

The light beam 609 generated by the light source 608 has a plurality of wavelengths (e.g., polychromatic light). Various light sources are known in the art, each generating light having a particular wavelength range. Because embodiments of the invention can be implemented over the entire spectral range from the UV (ultraviolet) to the Far IR (infrared), light source 608 is selected accordingly. For example, light source 608 comprises one or more of the following: argon lamp, xenon lamp, hydrogen lamp, deuterium lamp, tungsten lamp, arc lamp, hollow cathode lamp, Nernst glower, nichrome wire, globar, light emitting diodes (LED), and laser. According to the illustrated embodiment, the light source 608 is external to the spectrophotometry system 600 and is used in conjunction with the spectrophotometry system 600. In an alternative embodiment, the light source 608 is included in the spectrophotometry system 600 but external to the module 606. For example, the spectrophometry system 600 may include another module housing the light source 608 and the interferometer 602. Because the light source 608 has a location external to the module 606, potentially adverse effects of heat created by many types of light sources are avoided.

The interferometer 602 comprises a device that introduces interference effects into light waves of the input light beam 609 to yield the time dependent light power distribution in the input light beam 609. The interferometer 602 can have various configurations. For example, a Michelson interferometer is one configuration, which produces an interference pattern in an input light beam by splitting the light beam into two paths and reflecting the light beams back and recombining them.

Figure 7:
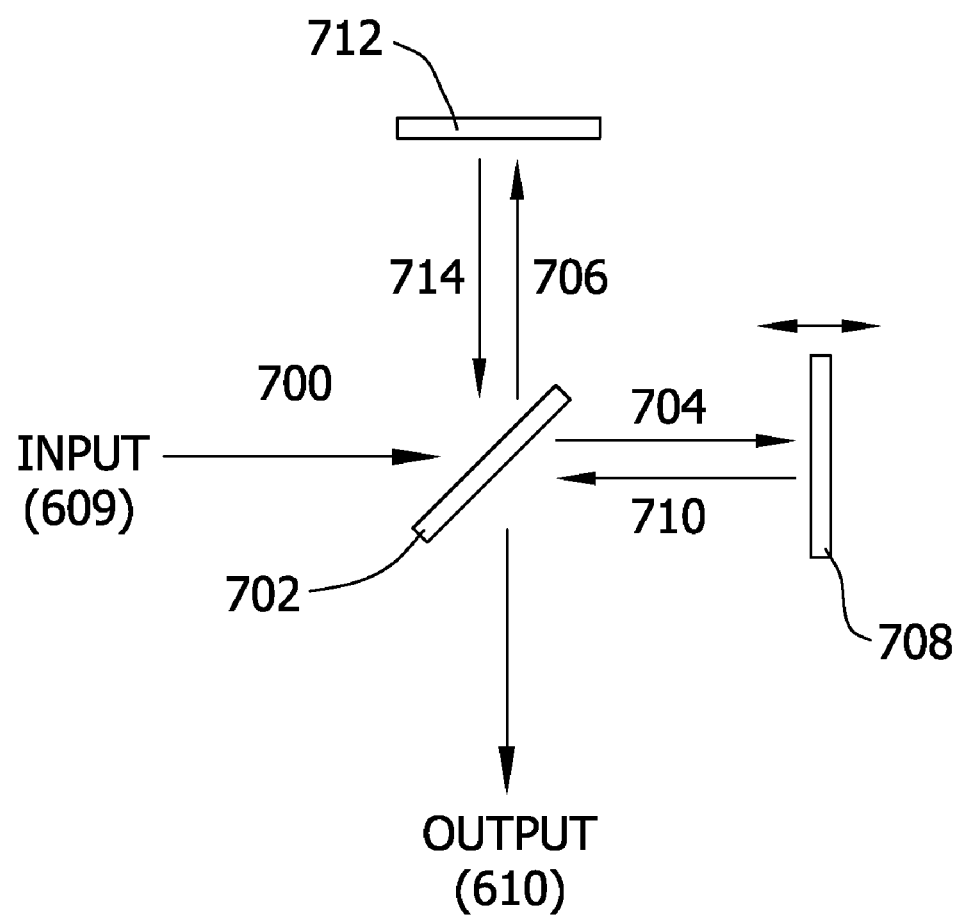
FIG. 7 is block diagram illustrating the operation of an interferometer according to an embodiment of the invention.

FIG. 7 illustrates operation of a Michelson Interferometer according to an embodiment of the present invention (e.g., the embodiment illustrated by FIG. 6). In particular, the input light beam 609 enters interferometer 602 from the left and strikes a beam splitter 702, which produces a transmitted beam 704 and a reflected beam 706. The transmitted beam 704 strikes a moving mirror 708 and is reflected back (beam 710) toward the beam splitter 702 in this embodiment. Likewise, the reflected beam 706 strikes a fixed mirror 712 and is reflected back (beam 714) toward the beam splitter 702. Beams 710 and 714 combine at beam splitter 702 in a manner described below to produce the interferometer output beam 610. Two beams, one denoted by vectors 704 and 710, and another denoted by vectors 706 and 714, initially emerge from beam splitter 702.

Each beam travels from the beam splitter 702, to a mirror (708, 712), and back again to the beam splitter 702. Beam-F, represented by beams 706 and 714, travels a fixed distance between beam splitter 702 and a fixed mirror 712. Beam-M, represented by beams 704 and 710, travels a variable distance between beam splitter 702 and a moving mirror 708 wherein the distance varies with the position of the moving mirror 708. The difference between the fixed and variable distances of travel is the retardation (δ). The retardation zero is defined as that position when both moving mirror 708 and fixed mirror 712 are exactly equidistant from the beam splitter 702. Thus, δ represents 2× the displacement of the moving mirror 708 from the equidistant position with respect to the fixed mirror 712.

According to the interferometer operation, the input light beam 609 is split via the beam splitter 702 to form the two beams, F and M. After being reflected by the fixed and moving mirrors (712 and 708), respectively, the F and M beams are recombined at the beam splitter 702, forming the interferometer output beam 610. Because the two beams F and M travel different distances, in general, there is a time-dependent phase difference between the F and M beams as they arrive back at the beam splitter 702. The time-dependent phase difference gives rise to interference effects in the interferometer output beam 610. In particular, each individual wavelength λ component of the input light beam 609 is modulated according to the expression ½ [1+cos(νt)], where the frequency ν is given by $$\nu = 2\frac{v_M}{\lambda}$$

where $v_M$ is the velocity of the moving mirror 708.

Because the input light beam 609 covers a range of wavelengths, the effect of the interferometer 602 on the total input light beam 609 can be described as a sum of the modulations for all the wavelength components in the input light beam 609. Thus, the output beam 610 has a complex pattern, referred to as an interferogram, encoding each frequency (or wavelength component) included in the input light beam 609. The interferogram is designated as I(δ), wherein I(δ)=$\Sigma_i I_i(\delta)$. For example δ=0 indicates that all frequencies in both F and M beams arrive back at the beam splitter 702 in phase. When this condition occurs, there is complete constructive interference for all of the wavelength components and the interferogram is a maximum, I(0).

Referring again to FIG. 6, the module 606 includes an optical system having a beam splitter 612 and a mirror 618, a sample detecting system 620, a reference detecting system 622, and an electronics module 640 having detector circuitry. The optical system receives the output beam 610 from the interferometer 602. In particular, the output beam 610 strikes the beam splitter 612. The beam splitter 612 splits the output beam 610 into a first beam 614 and a second beam 616 and directs the first beam 614 and the second beam 616 in separate paths. In particular, the first beam 614 is directed toward the sample detecting system 620 and the second beam 616 is directed toward the mirror 618. The mirror 618 redirects the second beam 616 toward the reference detecting system 622. Accordingly, the first beam 614 is broadly referred to as the sample beam (e.g., 614, 628) as it travels though the module 606. Similarly, the second 616 beam is broadly referred to as the reference beam (e.g., 616, 619, 630) as it travels through the module 606. The sample beam and the reference beam are the dual beams used for the noise cancellation.

The sample detecting system 620 includes a sample compartment 624 having a sample, and the reference detecting system 622 includes a reference compartment 626 having a reference. In an embodiment, the sample compartment 624 and/or reference compartment 626 additionally includes a cell (e.g., sample cell, reference cell) for containing the substance (e.g., sample, reference). The reference and sample are substances having the form of a solid, liquid or gas. The reference may be selected to have attributes based on the known attributes of the sample. For example, the reference may be a solid, liquid, or gas (including air) selected to have one or more components which are known to be missing from the sample. Due to the difference in components, the reference and the sample will interact (e.g., absorb, transmit, reflect, refract, etc.) differently with light at particular wavelengths. Accordingly, a comparison between the sample and the reference spectra reveals information about the particular components since the differences in the spectra are due to the particular components.

According to the embodiment illustrated in FIG. 6, the incident reference beam 619 interacts with the reference yielding an output reference beam 630 having a direction. For example, the incident reference beam 619 (or portions thereof) may be transmitted by the reference in a particular direction. Thus, the interaction (transmission) yields an output reference beam 630 comprising the transmitted reference beam (or portions thereof) having the particular direction (e.g., substantially the same direction as the direction of the incident reference beam 619). In another example, the incident reference beam 619 (or portions thereof) may be reflected by the reference in a particular direction (e.g., substantially opposite direction as the direction of the incident reference beam 619). Thus, the interaction (reflection) yields an output reference beam 630 comprising the reflected reference beam having the particular direction. In yet another example, a portion of the incident reference beam 619 may be transmitted by the reference in a first direction and another portion of the incident reference beam 619 may be reflected by the reference in a second direction. Thus, the interaction (transmission and reflection) yields an output reference beam 630 comprising the transmitted portion of the reference beam having the first direction and another output reference beam 630 comprising the reflected portion of the reference beam having the second direction.

Similarly, the incident sample beam 614 interacts with the sample yielding an output sample beam 628 having a direction. For example, the incident sample beam 614 (or portions thereof) may be transmitted by the sample in a particular direction. Thus, the interaction (transmission) yields an output sample beam 628 comprising the transmitted sample beam having the particular direction (e.g., substantially the same direction as the direction of the incident sample beam 614). In another example, the incident sample beam 614 (or portions thereof) may be reflected by the sample in a particular direction (e.g., substantially opposite direction as the direction of the incident sample beam 614). Thus, the interaction (reflection) yields an output sample beam 628 comprising the reflected sample beam having the particular direction. In yet another example, a portion of the incident sample beam 614 may be transmitted by the sample in a first direction and another portion of the incident sample beam 614 may be reflected by the sample in a second direction. Thus, the interaction (transmission and reflection) yields an output sample beam 628 comprising the transmitted portion of the sample beam having the first direction and another output sample beam 628 comprising the reflected portion of the sample beam having the second direction.

The reference detecting system 622 and the sample detecting system 620 each additionally include a detector (e.g., reference detector 634, sample detector 632) for detecting the output (e.g., sample or reference) beam 628, 630. In one embodiment, the detectors 628, 630 nearly exclusively sense AC components in the output beams 628, 630 to minimize effects caused by non-ideal behavior by beam splitter 702 of the interferometer 602 (appearing as DC components). For example, a non-ideal beam splitter 702 in the interferometer 602 results in beams 704 and 706 having unequal power. Accordingly, substantially all, if not all, of the power in the weaker beam is subject to the interference effects, while the excess power in the stronger beam remains unaffected by the interference effects. The beam splitter 702 splits the excess light power portion, which is essentially DC (e.g., slowly varying AC), so that a portion is included in the output beam 610 from the interferometer, and thus ultimately in the output (e.g., sample and reference) beams 628, 630. The light power without interference effects may carry noise which will likewise be included in the output beam from the interferometer 610, and thus be ultimately coherent in the output (e.g., sample and reference) beams 628, 630. By detecting only AC components in the output (e.g., sample or reference) beam 628, 630, the light power without interference effects is not used to obtain the optical spectrum (e.g., transmittance spectrum) for the sample. The detectors (632, 634) detect coherent noise carried by the light power without interference effects but the noise is canceled as further explained below.

The reference detector 634 substantially detects the output reference beam 630 based on the direction of the output reference beam 630. In one embodiment, the reference detector 634 substantially detects light having a direction indicative of light being transmitted by the reference. Thus, the reference detector 634 in this embodiment detects the output reference beam 630 if the output beam 630 comprises at least a portion of the transmitted reference beam. In another embodiment, the reference detector substantially detects light having a direction indicative of light being reflected by the reference. Thus, the reference detector 634 in this embodiment detects the output reference beam 630 if the output beam 630 comprises at least a portion of the reflected reference beam.

Similarly, the sample detector 632 substantially detects the output sample beam 628 based on the direction of the output sample beam 628. In one embodiment, the sample detector 632 substantially detects light having a direction indicative of light being transmitted by the sample. Thus, the sample detector 632 in this embodiment detects the output sample beam 628 if the output sample beam 628 comprises at least a portion of the transmitted sample beam. In another embodiment, the sample detector 632 substantially detects light having a direction indicative of light being reflected by the sample. Thus, the sample detector 632 in this embodiment detects the output sample beam 628 if the output beam 628 comprises at least a portion of the reflected sample beam.

Figure 8:
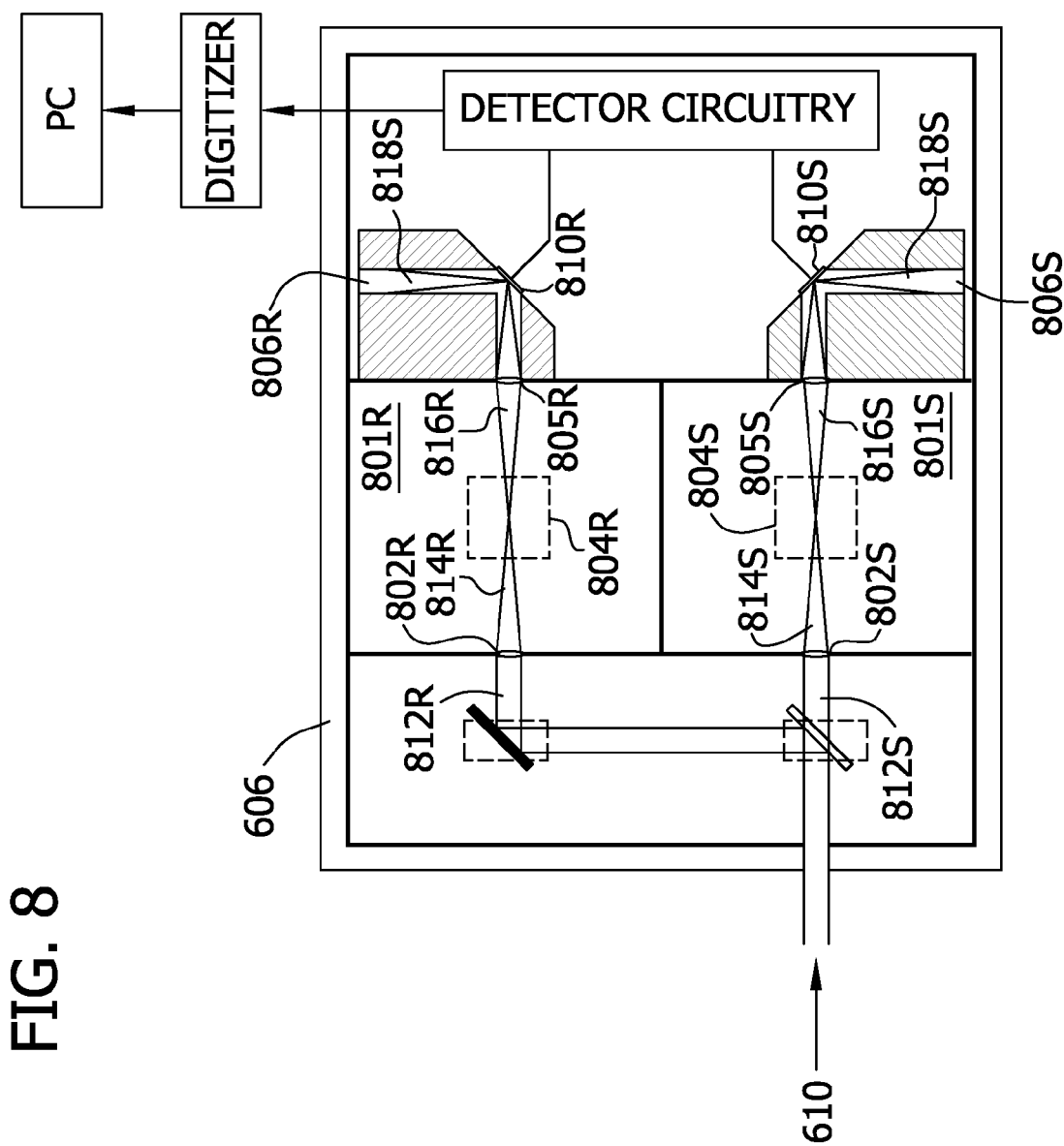
FIG. 8 is a block diagram illustrating a portion of a spectrophotometry system for detecting light transmitted by a sample and a reference according to an embodiment of the invention.

The reference detecting system 622 and the sample detecting system 620 may be configured to particularly accommodate the direction of the output beams 630, 628 being detected. Referring to FIG. 8, in one embodiment, the reference and sample detecting systems 622, 620 are configured to accommodate detecting light transmitted from the substances (e.g., reference, sample). The illustrated reference and sample detecting systems each include the compartment (e.g., sample compartment 801S, reference compartment 801R) and the detector (e.g., sample detector 810S, reference detector 810R) discussed above in FIG. 6. In addition, the detection system includes one or more of the following elements: first focusing lens 802, a second focusing lens 805, a cell for containing a substance 804, and a light trap 806. The elements are approximately oriented with respect to each other as illustrated. According to the detecting system, the (sample or reference) beam 812 enters the compartment 801 via the focusing lens 802 in a wall of the compartment 801. The focused beam enters the substance cell 804 and interacts with the substance therein. If the substance transmits the focused beam 814 (i.e., the focused beam 814 passes through the substance) or any portion thereof, an output beam 816 results comprising the transmitted focused beam (or portion thereof). Because transmitted beams have a direction passing through the substance 804, the detector 810 is located adjacent to the substance opposite to where the focused beam 814 enters the substance. After passing though the substance the output beam 816 passes though the second focusing lens 805 and strikes the detector 810. The output beam 816 strikes the detector 810 and the detector 810 reflects a portion of the output beam 818 which is directed to the light trap 806. The detector 810 is mounted at an angle (e.g., 45°) with respect to the general direction of the beam entering the compartment 801 in order to direct the reflected portion of the output beam 818 to the light trap 806. The light trap 806 traps the light. The trapped light may be analyzed for determining absorbance values.

Figure 9:
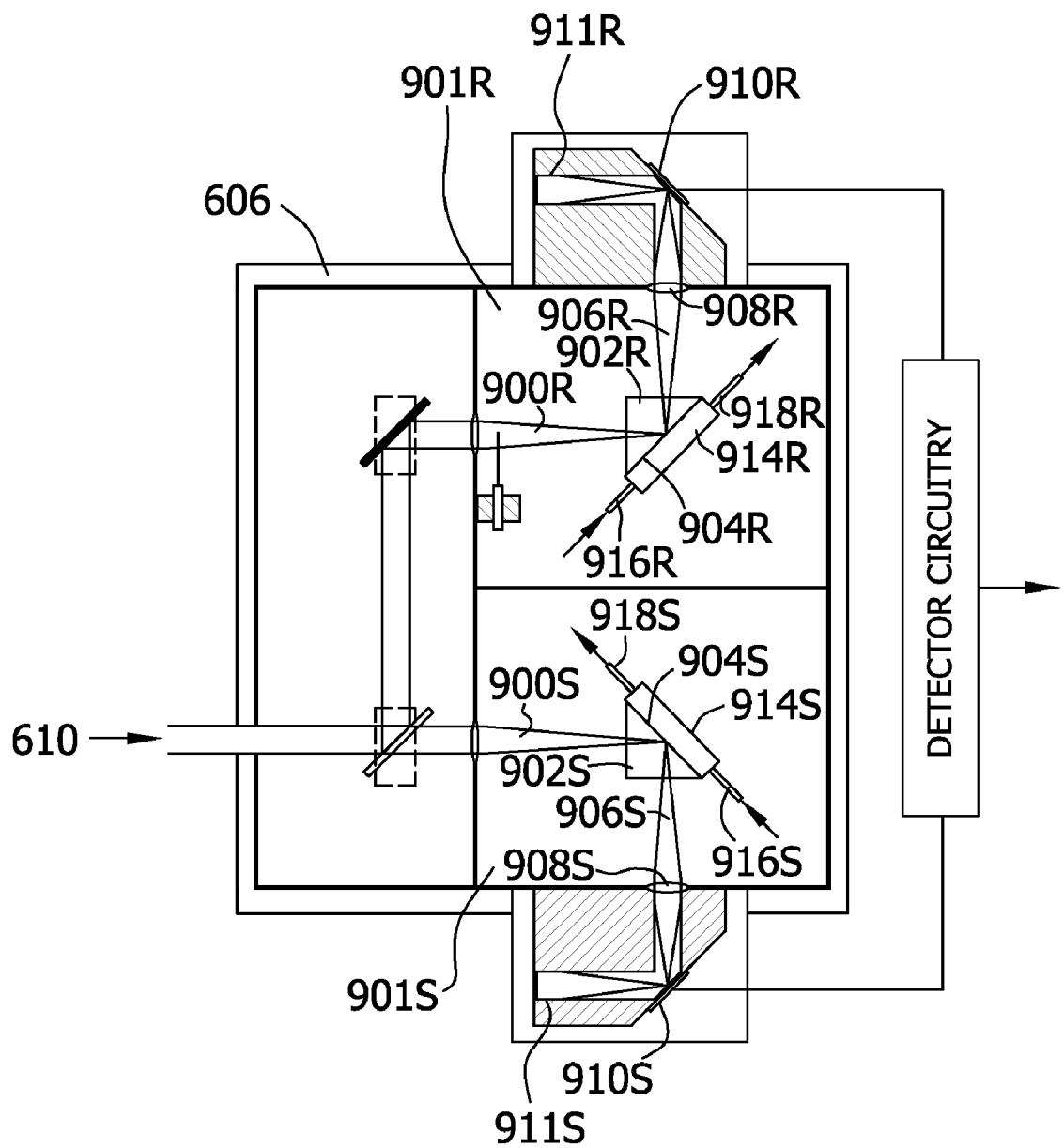
FIG. 9 is a block diagram illustrating a portion of a spectrophotometry system for detecting a signal internally reflected by a sample and for detecting a signal internally reflected by a reference according to an embodiment of the invention.

Referring to FIG. 9, in another embodiment, the reference and sample detecting systems 622, 620 are configured to accommodate detecting light internally reflected by the substances (e.g., reference, sample). Each of the illustrated reference and sample detecting systems includes the compartment (e.g., sample compartment 901S, reference compartment 901R) and the detector (e.g., sample detector 910S, reference detector 910R) discussed above in FIG. 6. In addition, the detecting system includes one or more of the following elements: an internal reflectance optical device (e.g., a prism 902 including an interaction surface 904), a focusing lens 908, a closed interaction volume 914 having an inlet 916 and an outlet 918 for delivering the substance (e.g., reference, sample) the interaction surface 904. According to the illustrated sample detecting system, after entering the sample compartment 901S (e.g., via a focusing lens) the sample beam 900S enters the prism 902S. The sample beam 900S travels through the prism 902S and strikes the interaction surface 904S wherein the sample is at or on the interaction surface 904S. The sample beam 900S interacts with the interaction surface 904S and the sample and thereby undergoes a total internal reflection. Accordingly, the output sample beam 906S comprises the sample beam 900S having an altered direction (e.g., rotated by 90°). The output sample beam 906S passes out of the prism, through the focusing lens 908S, and onto the sample detector 910S mounted in a chamber including a light trap 911S in the fashion (non-perpendicular) as described with respect to FIG. 8. The sample is delivered to the surface 904S with the closed sample volume 914S having the inlet 916S and the outlet 918S, both of which are connected to the exterior of the module 606 to allow a sample to be introduced into the sample compartment 901S without the need to open the module, which introduces baseline noise associated with airborne dust particles. In a similar fashion to the sample beam 901S the reference beam 901R interacts with the reference and is detected by the detector 910R.

Figure 10:
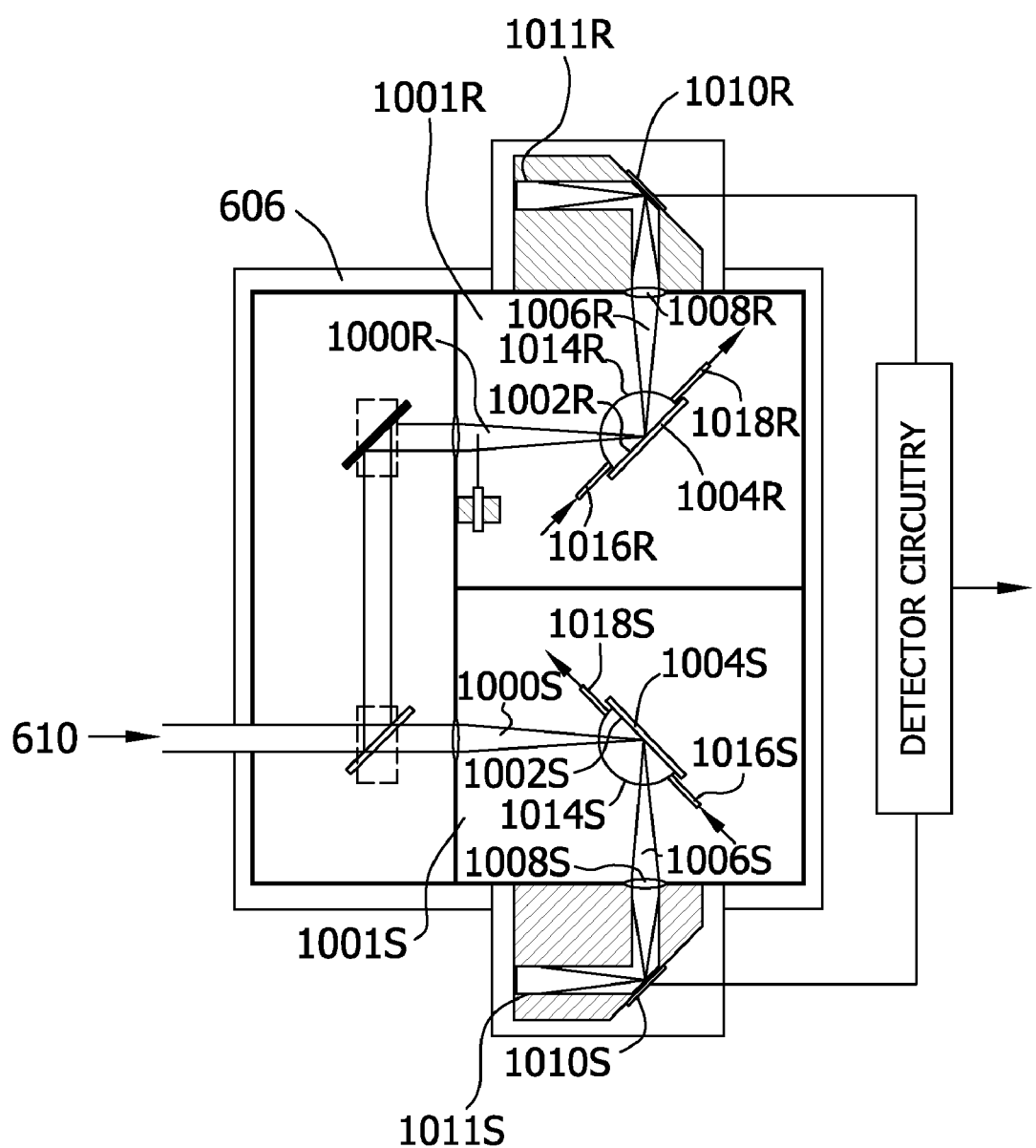
FIG. 10 is a block diagram illustrating a portion of a spectrophotometry system for detecting a signal specularly reflected by a sample and for detecting a signal specularly reflected by a reference according to an embodiment of the invention.

Referring to FIG. 10, in yet another embodiment, the reference and sample detecting systems 622, 620 are configured to accommodate detecting light specularly reflected by the substances (e.g., reference, sample). Each of the illustrated reference and sample detecting systems include the compartment (e.g., sample compartment 1001S, reference compartment 1001R) and the detector (e.g., sample detector 1010S, reference detector 1010R) generally discussed above in FIG. 6. In addition, the detecting system includes one or more of the following elements: a reflective interaction surface 1002 (e.g., mirror), a focusing lens 1008, a closed interaction volume 1014 having an inlet 1016 and an outlet 1018 for delivering the substance (e.g., reference, sample) on to the interaction surface 1002. According to the illustrated sample detecting system, the sample beam 1000S strikes the smooth reflective interaction surface 1002S of a wall 1004S. Interaction with a sample occurs at the interaction surface 1002S. In particular, the sample beam 1000S (or portion thereof) is specularly reflected by the sample resulting in an output beam 1006S. The output sample beam 1006S is focused by the focusing lens 1008S onto the sample detector 1010S mounted in a chamber including a light trap 1011S at a non-perpendicular angle to the incoming beam (as previously described with respect to FIG. 9). As indicated by FIG. 10, the angle of incidence with the interaction surface 1002S and the angle of reflection from the surface 1002S are both 45° so that the specular reflection process changes the direction of the sample beam by a total of 90°. However, various other angles can be used. A sample cell includes an optically transparent closed interaction volume 1014S that is sealed to and includes the wall 1004S as part of the interaction volume 1014S. An inlet 1016S and an outlet 1018S permit the introduction of sample into the interaction volume 1014S, as described with respect to FIG. 9. The solid wall 1004S forms one side of the interaction volume so that the reflective interaction surface 1002S may be in contact with sample. In particular, it is of interest to study absorption of light by substances from the gas phase that are attracted to and held on the interaction surface 1002S. In a similar fashion to the sample beam 1000S, the reference beam 1000R interacts with the reference and is detected by the detector 1010R.

Figure 11:
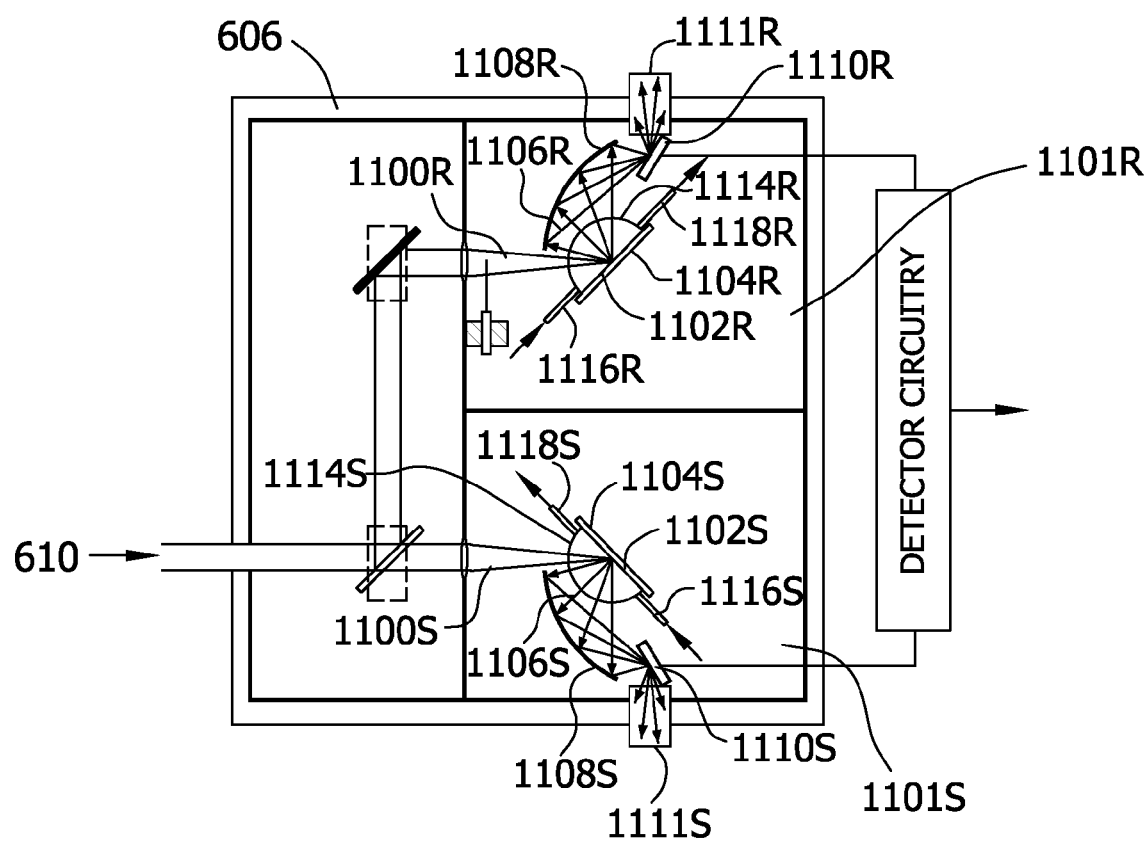
FIG. 11 is a block diagram illustrating a portion of a spectrophotometry system for detecting a signal diffusely reflected by a sample and for detecting a signal diffusely reflected by a reference according to an embodiment of the invention.

Referring to FIG. 11, in yet another embodiment, the reference and sample detecting systems 622, 620 are configured to accommodate detecting light diffusely reflected from the substances (e.g., reference, sample). Each of the illustrated reference and sample detecting systems includes the compartment (e.g., sample compartment 1101S, reference compartment 1101R) and the detector (e.g., sample detector 1110S, reference detector 1110R) generally discussed above in FIG. 6. In addition, the detecting system includes one or more of the following elements: a matte interaction surface 1102, a focusing mirror 1108, a closed interaction volume 1114 having an inlet 1116 and an outlet 1118 for delivering the substance (e.g., reference, sample) the interaction surface 1102. Referring to the illustrated sample detecting system, the sample beam 1100S enters the sample compartment 1101S and strikes a matte interaction surface 1102S of a wall 1104S. Light is scattered over a range of directions, as indicated by arrows. The output sample beam comprises a portion 1106S of the scattered light which is focused by the mirror 1108S onto the sample detector 1110S mounted in a chamber including a light trap 1111S. A closed sample interaction volume 1114S is completed on one side by the wall 11104S so that sample supplied via inlet 1116S and outlet 1118S may interact with the interaction surface 1102S as previously described with respect to FIG. 9. In a similar fashion to the sample beam 1100S, the reference beam 1100R interacts with the reference and is detected by the detector 1110R.

Referring again to FIG. 6, the reference and sample detectors 634, 632 each generate a signal representative of the detected portion of the respective, reference or sample, beam. In one embodiment, the reference and sample detectors 634, 632 each generate a current that varies in precise proportion to the power of an output (reference or sample) beam (630, 628). For example, reference and sample detectors 634, 632 each include a photodiode detector or the like for detecting light producing photocurrents. In an alternate embodiment, the reference and sample detectors 634, 632 each generate a voltage that varies in precise proportion to the power of an output (reference or sample) beam (630, 628). For example, reference and sample detectors 634, 632 include integral buffer amplifiers, for example, that output a voltage. Other exemplary detectors include: photomultipliers, phototubes, photocells, charge transfer conductor, thermocouples, bolometers, pyroelectric cells, and/or infrared detectors.

The reference and sample signals generated by the reference and sample detectors 638, 636 are transmitted to the electronics module 640. The electronics module 640 includes a detector circuit for producing a reference voltage proportional to the reference signal 638, a sample voltage proportional to the sample signal 636, and a difference voltage proportional to the difference between the reference signal 638 and the sample signal 636. Additionally, the electronics module includes a first converter and a second converter. The converters are also referred to as digitizers. The first converter converts the difference voltage at predefined intervals from an analog signal to a digital signal. The second converter converts the reference voltage at the predefined intervals from an analog signal to a digital signal. The first converter and the second converter simultaneously (i.e., substantially simultaneously) convert the difference voltage and the reference voltage. The substantially simultaneous conversion of the difference and reference voltages advantageously minimizes the effect of drift. The digital difference signal and the digital reference signal 642 are transmitted to a processor 644 (e.g., microprocessor, computer, controller, etc.).

The processor 644 is configured in one embodiment to determine a spectrum of the sample based on the digital difference signal (i.e. the difference voltage). In this embodiment, the processor 644 is configured to determine the transmittance spectrum of the sample based on the digital difference signal and the digital reference signal. In particular, the processor 644 determines a difference interferogram $I_D(\delta)$ from the digital difference signal. Likewise, the processor 644 determines a reference interferogram (i.e., background interferogram) $I_R(\delta)$ from the digital reference signal. The difference interferogram and the reference interferogram are related as follows: $I_D(\delta)=I_S(\delta)-I_R(\delta)$, where $I_S(\delta)$ is the sample interferogram. The processor 644 calculates the Fourier Transform of $I_D(\delta)$ yielding $DFT\{I_D(\delta)\}=DFT\{I_S(\delta)\}-DFT\{I_R(\delta)\}=G_S(v)-G_R(v)$. Additionally, the processor 644 calculates the Fourier Transform of $I_R(\delta)$ yielding $DFT\{I_R(\delta)\}=G_R(v)$. Thus, the processor 644 obtains the background spectrum $G_B(v)=G_R(v)$. Since $DFT\{I_D(\delta)\}/DFT\{I_R(\delta)\}=[G_S(v)-G_R(v)]/G_R(v)$, the transmittance spectrum $[GS(v)/GR(v)]$ is obtained according to the following relationship $$\frac{G_S(v) - G_R(v)}{G_R(v)} + 1,$$

alternatively denoted as $$\frac{DFT\{I_D(\delta)\}}{DFT\{I_R(\delta)\}} + 1.$$

The notation implies that the processor 644 divides pointwise for every discrete frequency represented in $G(v)$. In another embodiment, the second converter converts the sample voltage signal to a digital sample signal and the processor 644 is configured to determine a spectrum of the sample based on the digital difference signal and the digital sample signal. In yet another embodiment, the electronics module further includes a third converter for converting the sample voltage signal to a digital signal and the processor 644 is configured to determine a spectrum of the sample based on the digital difference signal and, the digital reference signal and/or the digital sample signal.

Because the spectrum is obtained from the digital difference signal, coherent noise included in the digital reference signal and the digital sample signal is substantially canceled. For example, according to the embodiment 600 illustrated in FIG. 6, the output beam from the interferometer 610 is delivered to the module 606 and split into a first and a second beam (614 and 616) by the beam splitter 612. Noise included in the interferometer output is thus coherent in the sample and reference beams (614, 619) interacting with the sample and the reference. Likewise, the coherent noise will be present in both output beams (630, 628) detected by the detectors (634, 632). Since the coherent noise is detected by both detectors 634, 632, the noise is substantially canceled in the difference interferogram $I_D(\delta)$. Additionally, the noise inherent in the digitization process is minimized as a result of obtaining the spectrum from the digital difference signal. As discussed above, digitization errors (i.e., noise) depend on bandwidth and resolution (and additional factors). In particular, digitization errors are a result of the finite resolution of the digitizer (i.e., electronics module 640, e.g., converter) limiting the ability of the digitizer to digitize the signals generated by the detector with sufficient precision to indicate relatively small absorption peaks. Obtaining the spectrum from the digital difference signal minimizes the required digitizer resolution because it is a relatively small signal (difference of two nearly identical output signals). Thus the large central signal, or "burst", (e.g., FIG. 4) is reduced to a much smaller signal. $I_D(\delta)$ for the background can be made very small and with weakly absorbing samples, $I_D(\delta)$ for the sample will also be very small, containing only weak oscillations from both sample and residual background. Therefore, the digital resolution required for $I_D(\delta)$ is relatively low. For example, it is likely between 10-fold and 100-fold lower than that for $I_R(\delta)$ or $I_S(\delta)$. Thus, the digitization noise is effectively eliminated in $I_D(\delta)$ Additional embodiments of the present invention discussed below include features for further increasing the signal to noise ratio in optical spectra obtained by the spectrophotometry system 600 of the present invention. The features may be applied, individually or in combination, to the spectrophotometry system 600 described above. One additional embodiment includes features for balancing the reference and sample beams to optimize noise cancellation. As previously noted, $I_D(\delta)=I_S(\delta)-I_R(\delta)$. Thus, the degree of noise cancellation increases as $I_D(\delta)$ decreases. In the limit $I_D(\delta) \to 0$, coherent noise is completely canceled. The additional embodiments contemplate balancing the detector signals. By comparing (1) the transmittance spectrum $$\left( \frac{G_S(v)}{G_R(v)} = \frac{DFT\{I_S(\delta)\}}{DFT\{I_R(\delta)\}} \right)$$

obtained from the sample and reference interferograms, to (2) the transmittance spectrum $$\left( \frac{G_S(v) - G_R(v)}{G_R(v)} + 1 = \frac{DFT\{I_D(\delta)\}}{DFT\{I_R(\delta)\}} + 1 \right),$$

obtained using the difference and reference interferograms, it is apparent that the degree of coherent noise cancellation equals the degree of balance of the detector signals. In particular, the noise in the transmittance spectrum $G_S(v)/G_R(v)$ is given by its RMS (root mean square) deviation, $\sigma$. The noise for the transmittance spectrum obtained by the standard method (i.e., transmittance spectrum based on $V_S$ and $V_R$) is denoted $\sigma(SM)$. This noise is assessed from the transmittance equation (1) based on assumptions that $\sigma(G_S)/G_S=\sigma(V_S)/V_S$ and $\sigma(G_R)/G_R=\sigma(V_R)/V_R$. Here the terms $\sigma(G_S)$, $\sigma(G_R)$, $\sigma(V_S)$, and $\sigma(V_R)$ refer to RMS deviations in the sample spectrum, reference spectrum, voltage reading for the sample and voltage reading for the reference, respectively. From equation 1 we obtain, $$\sigma(SM) = |(G_S/G_R)|[(\sigma(G_S)/G_S)^2 + (\sigma(G_R)/G_R)^2]^{1/2}$$

$$= |(V_S/V_R)|[(\sigma(V_S)/V_S)^2 + (\sigma(V_R)/V_R)^2]^{1/2}$$

Since $V_S \approx V_R$, $\sigma(SM)=2^{1/2}|\sigma(V_R)/V_R|$

The RMS noise for the noise cancellation method described by aspects of the present invention (i.e., transmittance spectrum based on $V_D$) is denoted $\sigma(NC)$. From the transmittance equation (2) and with the same assumptions used above, we obtain, $$\sigma(NC)=|(V_D/V_R)|[(\sigma(V_D)/V_D)^2+(\sigma(V_R)/V_R)^2]^{1/2}$$

With an additional assumption that for noise cancellation, the difference voltage is related to the background voltage noise by $|\sigma(V_D)/V_D|=|\sigma(V_R)/V_R|$, the RMS noise for the noise cancellation method is given by $$\sigma(NC) \approx |(V_D/V_R)|2^{1/2}[\sigma(V_R)/V_R]$$

The noise reduction factor is represented as $\sigma(NC)/\sigma(SM)$ and substitution from the equations above shows that the noise reduction factor is $|(V_D/V_R)|$.

We note that even if the techniques of multiple scanning and signal averaging are applied to minimize the noise in the background signal, the same noise reduction factor applies.

Embodiments of the present invention contemplate various balancing protocols. In the most important embodiment, the balancing protocol is designed to enable the observance of very small peaks, normally obscured by noise. In such an application, the background signals are balanced so that $V_D \approx 0$. This is accomplished e.g., with the circuitry shown in FIG. 13, by adjusting potentiometer 1310 until $V_D \approx 0$. The high degree of balance will also be retained in the sample spectrum since the absorbance effects (peaks) are extremely small. Thus, according to the embodiment, the signals are balanced so that the background interferogram is minimized, and as a result, noise cancellation in the background spectrum is maximized. In addition, since the sample signals are also very nearly minimized for the sample interferogram, a high degree of noise cancellation in the sample spectrum is achieved here as well. Consequently a high degree of noise cancellation will be present in the calculated transmittance spectra.

Each detector signal depends on both beam power and detector sensitivity. In practice, the detector signals may be slightly different, in which case some adjustment may be required to attain the required degree of signal balance. For example, a 10-fold noise reduction will require a signal imbalance of 10% or less, whereas a 100-fold noise reduction will require a signal imbalance of 1% or less. Balancing the detector signals can be accomplished by partially blocking the stronger beam and/or by incorporating adjustment features in the electronics module 640, as described below.

Figure 12:
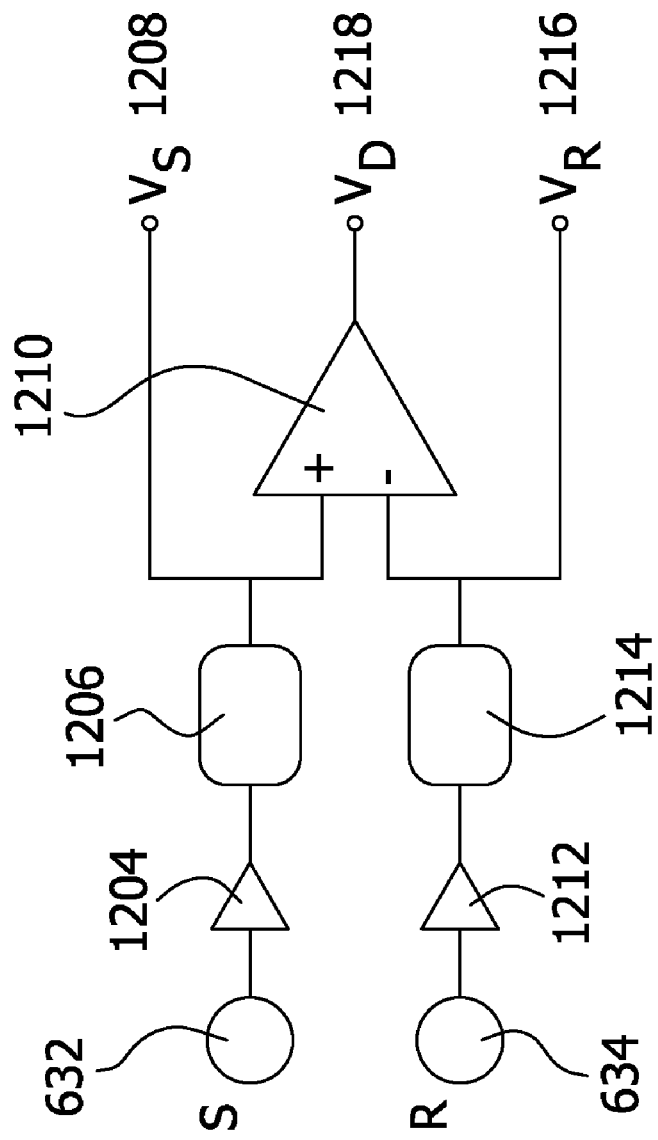
FIG. 12 is a block diagram illustrating circuitry for balancing a sample voltage signal and a reference voltage signal in a spectrophotometry system according to an embodiment of the invention.

Referring to FIGS. 6 and 12, in yet another embodiment, the sample and reference signals are balanced in "voltage mode." In particular, the electronics module 640 further includes a sample amplifier 1204, a sample filter (e.g., variable gain component) 1206, a reference amplifier 1212, a reference filter (e.g., variable gain component) 1214, and a difference amplifier 1210. According to the circuitry illustrated by FIG. 12, the signals 638, 636 generated by the reference and sample detectors 634, 632 are voltage signals. The voltage signal 638 generated by the reference detector 634 is amplified by the reference amplifier 1212 and adjusted by the reference filter 1214 to achieve a pre-determined degree of signal balance. The adjusted reference voltage signal ($V_R$) 1216 is transmitted via the converter (e.g., second converter) to the processor 644 for obtaining $I_R(\delta)$. The adjusted reference voltage signal $V_R$ 1216 is also transmitted to an inverting input of the difference amplifier 1210. The voltage signal 636 generated by the sample detector 632 is amplified by the sample amplifier 1204 and adjusted by the sample filter 1206 to achieve a pre-determined degree of signal balance. The adjusted sample voltage signal ($V_S$) 1208 is transmitted to a non-inverting input of the difference amplifier 1210. The difference amplifier 1210 generates the difference voltage ($V_D$) 1218. The difference voltage ($V_D$) 1218 is transmitted via the first converter to the processor 644 for obtaining $I_D(\delta)$. In another embodiment, the adjusted sample voltage signal ($V_S$) 1208 is additionally transmitted via the converter (e.g., third converter) to the processor 644 for obtaining $I_S(\delta)$.

Figure 13:
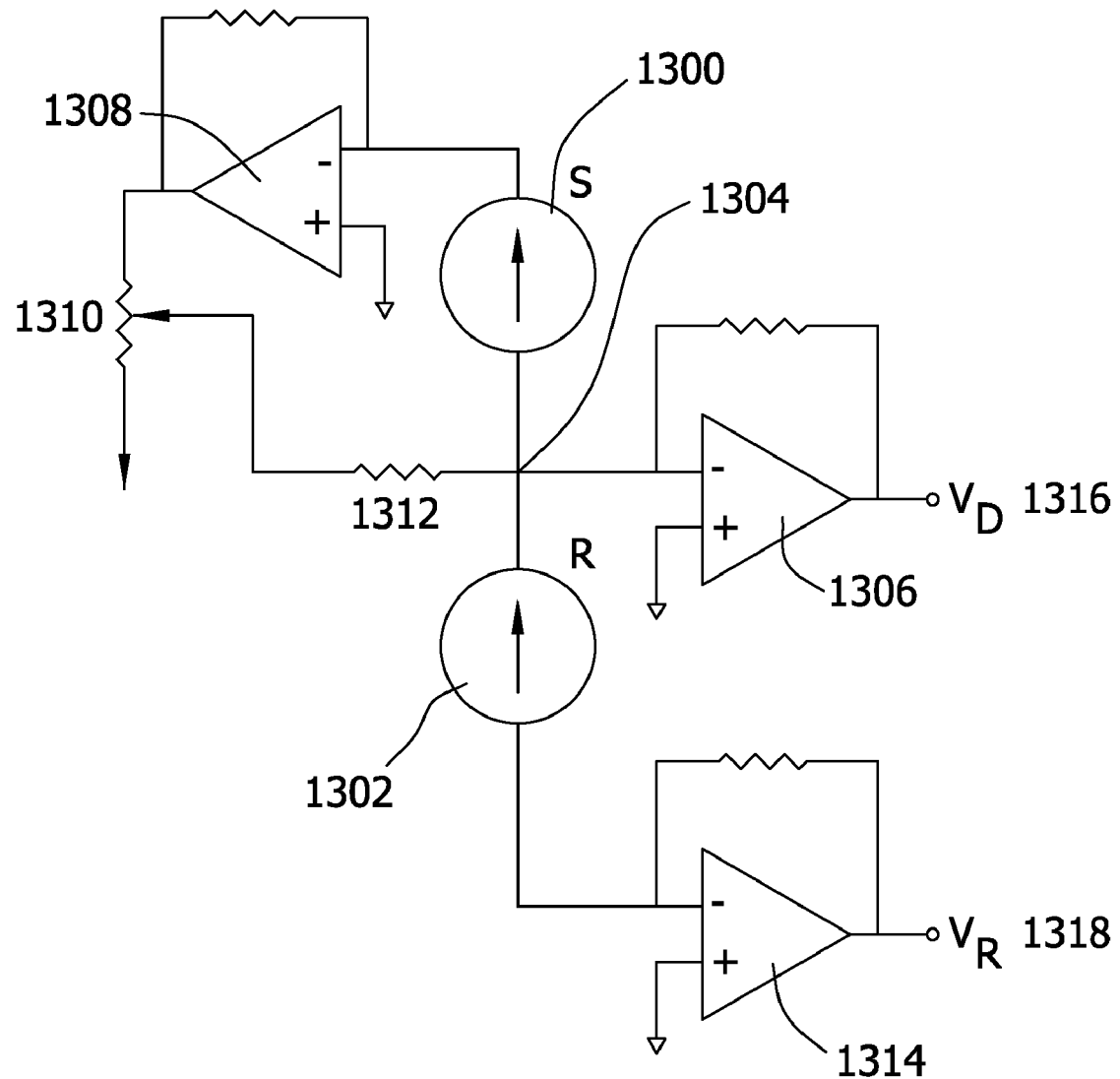
FIG. 13 is a block diagram illustrating circuitry for balancing a sample current signal and a reference current signal in a spectrophotometry system according to an embodiment of the invention.

Referring to FIGS. 6 and 13, in another additional embodiment, the sample and reference signals are balanced in "current mode." In particular, the electronics module 640 further includes a summing point 1304, three current to voltage amplifiers (i.e., first 1306, second 1314, and third 1308), a potentiometer 1310, and a resistor 1312. According the embodiment, the signals 638, 636 generated by the reference and sample detectors 634, 632 (e.g., photodiodes) are current signals (e.g., photocurrents) which are effectively subtracted at the summing point 1304 yielding the difference current $I_D$. The difference current $I_D$ is transmitted to an inverting input of the first current to voltage amplifier 1306 yielding $V_D$ 1316. Additionally, the reference current $I_R$ is transmitted to the second current to voltage amplifier 1314 yielding reference voltage $V_R$ 1318. The reference and sample signals 638, 636 are balanced by transmitting the current signal generated by the sample detector 632 to the third current to voltage amplifier 1308, yielding an output voltage. The output voltage is dropped across the potentiometer 1310 and transmitted as an additional current through the resistor 1312 to the summing point 1304. The additional current supplements the current generated by the sample detector ($I_S$). Accordingly, the potentiometer 1310 is adjusted to balance $I_S$ and $I_R$ (the current generated by the reference detector). The configuration of the electronics module illustrated by FIG. 13 is designed for balancing the detector signals 638, 636 when the sample current 636 is less than the reference current 638. In another embodiment, the configuration of the electronics module is designed for balancing the detector signals 638, 636 when the sample current 636 is greater than the reference current 638. This is accomplished by a straightforward modification of the FIG. 13 circuitry.

Figure 14:
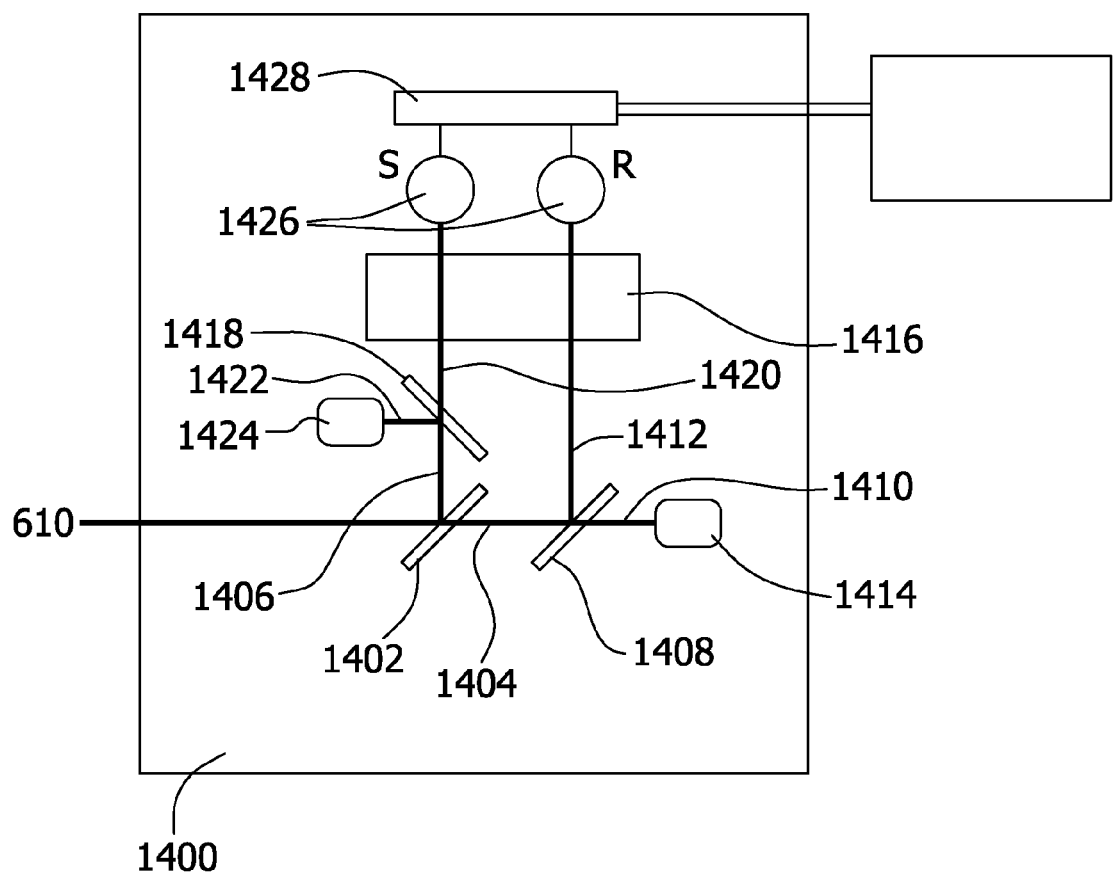
FIG. 14 is a block diagram illustrating a spectrophotometry system having a triple beam splitter configuration according to an embodiment of the invention.

FIG. 14 illustrates an additional embodiment wherein the optical system further includes a triple beam splitter configuration for balancing the reference and sample beams and further optimizing the coherent noise cancellation. Noise cancellation as described above assumes that the component(s) (e.g., beam splitter) splitting the output beam 610 from the interferometer 602 into the first and second beams (614, 616) have a wavelength-independent 50:50 splitting ratio. This may be difficult to achieve with a single beam splitter as it requires the beam splitter to be ideal. The illustrated embodiment provides a configuration using three matched beam splitters which produces a substantially wavelength-independent 50:50 splitting ratio.

In the embodiment illustrated in FIG. 14, the module 606 further includes second and third beam splitters, and first and second light traps, in addition to the first beam splitter 612 (illustrated here as 1402). The mirror 618 is not needed in this embodiment. As illustrated, the module 606 is configured to accommodate the additional elements. The first 1402, second 1408, and third 1418 beam splitters are substantially matched. According to the illustrated embodiment, the output beam 610 from the interferometer 602 enters the module 1400 (e.g., from a direction left of the module 1400). The output beam 610 strikes the first beam splitter 1402 (e.g., at an angle of incidence of 45°), which produces a first transmitted beam 1404 and a first reflected beam 1406. The first transmitted beam 1406 strikes the second beam splitter 1408 (e.g., at an angle of incidence of 45°), which produces a second transmitted beam 1410 and a second reflected beam 1412. The second transmitted beam 1410 is captured in the first light trap 1414. The second reflected beam 1412 enters the reference detecting system 1416. The first reflected beam 1406 strikes a third beam splitter 1418 (e.g., at an angle of incidence of 45°), which produces a third transmitted beam 1420 and a third reflected beam 1422. The third reflected beam 1422 is captured in the second light trap 1424. The third transmitted beam 1420 enters the sample detecting system 1416. The second reflected beam 1412 and the third transmitted beam 1420 strike sample and reference detectors 1426.

The use of three beam splitters in the illustrated embodiment results in the loss of more than half the light power present in the output beam from the interferometer. The exact amount depends upon the characteristics of the particular beam splitters. Beam splitters with near 50/50 (T/R) splitting ratio minimize the light loss. Despite the loss of light, the triple beam splitter configuration has the great advantage that with three matched beam splitters, the two emergent beams (e.g., the second reflected beam 1412 and the third transmitted beam 1420) will be of equal power at all wavelengths. Additionally, the two emergent beams (e.g., the second reflected beam 1412 and the third transmitted beam 1420) also have equal polarization and phase at all wavelengths. This greatly simplifies the balancing of the reference and sample beams. Preliminary measurements and calculations indicate that under realizable conditions (machining tolerances and commercial beam splitters), the beam powers will differ by much less than 0.5% over the entire range of wavelength from UV to far IR, which is sufficient to ensure source noise cancellation to well below the shot noise limit of the detectors (e.g., photodiodes).

In another additional embodiment, alternative to the first 1402, second 1408, and third 1418 beam splitters the module includes a mirror prism for balancing the reference and sample beams and further optimizing the coherent noise cancellation. According to the embodiment, the output beam is divided by reflections from two-mirrored surfaces of the prism into a first and second beam of nominally equal power. The first and second beams diverge by 180°. Accordingly, first and second mirrors are located to reflect the first and second beams redirecting the first and second beams in parallel directions. Because of potential scattering of light by the apex, that region of the mirror prism is shielded from the output beam. The power ratio of the first and second beams can be adjusted by moving the prism or by particularly locating apertures.

According to another additional embodiment, the moving mirror tracking error identified above is minimized. Moving mirror tracking error causes noise in the abscissas of both $I_D(\delta)$ and $I_R(\delta)$. Multiplying the error at any given instant by the instantaneous slope $[dI_D(\delta)/d(\delta)]$ gives the ordinate error at that instant. Qualitatively, if the magnitude of the $I_D(\delta)$ ordinate is dramatically decreased as with cancellation, the instantaneous slope $[dI_D(\delta)/d(\delta)]$ will be correspondingly decreased, giving a large reduction in the coherent noise level of $I_D(\delta)$.

According to another embodiment, signal averaging of multiple scans is used to reduce noise from various sources. Signal averaging improves signal to noise ratio proportional to $N^{1/2}$, where N is the number of scans averaged. For example, to improve the signal to noise ratio by 10-fold, 100 scans are averaged. Advantageously, the cancellation methodology described above reduces coherent noise, so that a given signal to noise ratio can be attained with fewer scans than with known FT instrumentation. Thus, the present invention, for any given time period for data acquisition, achieves better ultimate signal to noise ratio. Additionally, fast processes can be studied with the present invention since spectra can be obtained more rapidly allowing spectral changes to be seen on a shorter time scale.

According to aspects of the invention, the module (e.g., sealed housing) 606 is constructed to minimize thermal drift. Unitary housing construction can provide a compact, mechanically and thermally stable device in accordance with the invention and apply any of the types of measurement discussed above. Thermal stabilization is achieved primarily from a unitary solid metal housing. A material having a high heat conductivity, e.g. Aluminum, is used. A hollowed portion is carved out in a shape and depth to provide for the mounting and placement of device components. A cover plate of solid metal seals the housing, which is insulated on all sides, including the cover plate. Excellent mechanical stability is also provided by the unitary structure of the housing. The solid unitary metal housing can provide relatively large thermal mass in a compact package, permitting a relatively compact (i.e., small) device.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A spectrophotometry system comprising:
   an interferometer for receiving, from a light source, a source light beam and introducing interference effects thereto;
   a sealed housing for receiving, from the interferometer, the source light beam having the interference effects;
   an optical system within the housing for splitting the source light beam having the interference effects into a reference beam and a sample beam and for directing the reference beam and the sample beam in separate paths;
   a reference compartment within the housing, said reference compartment including a reference for interacting with the reference beam wherein said interacting yields an output reference beam having a direction;
   a reference light detector for detecting at least a portion of the output reference beam based on the direction of the output reference beam and generating a reference signal representative of the detected light;
   a sample compartment within the housing, said sample compartment including a sample for interacting with the sample beam wherein said interacting yields an output sample beam having a direction;
   a sample light detector for detecting at least a portion of the output sample beam based on the direction of the output sample beam and generating a sample signal representative of the detected light;
   a detector circuit for producing a reference voltage proportional to the reference signal and a difference voltage proportional to the difference between the reference signal and the sample signal; and
   a processor configured to determine a spectrum of the sample based on the difference voltage, wherein said processor is configured to generate an interferogram from the difference voltage and to calculate a Fourier Transform of the interferogram, said spectrum being a function of the Fourier Transform of the interferogram.

2. The spectrophotometry system of claim 1 wherein the processor is further configured to determine the spectrum of the sample based on the reference voltage.

3. The spectrophotometry system of claim 1 wherein the processor is further configured to determine the spectrum of the sample based on the sample voltage.

4. The spectrophotometry system of claim 1 wherein the reference reflects at least a portion of the reference beam at a particular direction and the output reference beam comprises said reflected portion of the reference beam having said particular direction.

5. The spectrophotometry system of claim 1 the reference transmits at least a portion of the reference beam at a particular direction and the output reference beam comprises said transmitted portion of the reference beam having said particular direction.

6. The spectrophotometry system of claim 1 wherein the sample reflects at least a portion of the sample beam at a particular direction and the output sample beam comprises said reflected portion of the sample beam having said particular direction.

7. The spectrophotometry system of claim 1 the sample transmits at least a portion of the sample beam at a particular direction and the output sample beam comprises said transmitted portion of the sample beam having said particular direction.

8. The spectrophotometry system of claim 1 wherein the detector circuit includes a variable gain component, said variable gain component balancing the reference signal and the sample signal.

9. The spectrophotometry system of claim 1 wherein the detector circuit includes a summing point having feedback to balance the reference signal and the sample signal.

10. The spectrophotometry system of claim 1 further comprising:
- a first converter for converting the difference voltage at predefined intervals from an analog signal to a digital signal;
- a second converter for converting the reference voltage at the predefined intervals from an analog signal to a digital signal; and
- a third converter for converting the sample voltage at the predefined intervals from an analog signal to a digital signal.

11. A spectrophotometry device, comprising:
- a Michelson interferometer for receiving, from a light source, a source light beam and introducing interference effects thereto;
- a sealed housing;
- a first beam splitter within the housing and in optical communication with the output of the interferometer, said first beam splitter having a transmissive side and a reflective side;
- a second beam splitter within the housing and in optical communication with the transmissive side of said first beam splitter;
- a third beam splitter within the housing and in optical communication with the reflective side of said first beam splitter;
- a reference detecting system within the housing and in optical communication with one of said second and third beam splitters; and
- a sample detecting system within the housing and in optical communication with the other of said second and third beam splitters.

12. The spectrophotometry device of claim 11, wherein said reference and said sample detecting systems are in optical communication with a reflective side of said second beam splitter and a transmissive side of said third beam splitter.

13. The spectrophotometry device of claim 11, further comprising light traps formed as part of said hollow portion and disposed to trap light transmitted from the second beam splitter and reflected light from said third beam splitter.

14. The spectrophotometry device of claim 11, further comprising additional light traps to trap reflected light from said reference and sample detecting systems.

15. The spectrophotometry device of claim 11, wherein said reference and said sample detecting systems each comprise:
- a prism including an interaction surface;
- a detector;
- a lens that focuses a beam output from said prism onto said detector; and
- a closed interaction volume having an inlet and an outlet for delivering gas or liquid to the interaction surface.

16. The spectrophotometry device of claim 11, wherein said reference and said sample detecting systems each comprise:
- a reflective interaction surface;
- a detector;
- a lens that focuses a beam output from said reflective interaction surface onto said detector; and
- a closed interaction volume having an inlet and an outlet for delivering gas or liquid to the reflective interaction surface.

17. The spectrophotometry device of claim 11, wherein said reference and said sample detecting systems each comprise:
- a matte interaction surface;
- a detector;
- a lens or mirror that focuses scattering output from said matte interaction surface onto said detector; and
- a closed interaction volume having an inlet and an outlet for delivering gas or liquid to the interaction surface.

18. A method of determining an optical spectrum for a sample substance, said method comprising:
- receiving a source beam from an external light source, said source beam comprising having a plurality of wavelengths;
- introducing interference effects into the source beam;
- splitting the source beam comprising the interference effects into a reference beam and a sample beam;
- directing the reference beam into a reference cell having a reference substance therein, said reference substance interacting with the reference beam, said interacting yielding an output reference beam having a direction;
- directing the sample beam into a sample cell having the sample substance therein, said sample substance interacting with the sample beam, said interacting yielding an output sample beam having a direction;
- detecting at least a portion of the output reference beam and at least a portion of the output sample beam;
- generating a reference signal representative of the detected portion of the output reference beam and a sample signal representative of the detected portion of the output sample beam;
- generating a reference voltage proportional to the reference signal and a difference voltage proportional to the difference between the reference signal the sample signal;
- generating an interferogram from the difference voltage;
- calculating a Fourier Transform of the interferogram; and
- determining a spectrum of the sample as a function of the calculated Fourier Transform of the interferogram.

* * * * *